United States Patent
Wakayama et al.

(10) Patent No.: US 10,213,319 B2
(45) Date of Patent: Feb. 26, 2019

(54) NAVIGATION DEVICE FOR JOINT REPLACEMENT AND SURGICAL SUPPORT DEVICE

(71) Applicants: ARTHRODESIGN. LTD., Kawaguchi-shi, Saitama (JP); LEXI CO., LTD., Toshima-ku, Tokyo (JP); SAITAMA MEDICAL UNIVERSITY, Iruma-gun, Saitama (JP)

(72) Inventors: Toshitaka Wakayama, Saitama (JP); Yukari Kito, Kawaguchi (JP); Norio Seitoku, Tokyo (JP); Takashi Handa, Kawaguchi (JP); Toru Yoshizawa, Saitama (JP)

(73) Assignees: ARTHRODESIGN, LTD., Kawaguchi-Shi, Saitama (JP); LEXI CO., LTD., Tokyo (JP); SAITAMA MEDICAL UNIVERSITY, Iruma-Gun, Saitama (JP)

( * ) Notice: Subject to any disclaimer, the term of this patent is extended or adjusted under 35 U.S.C. 154(b) by 781 days.

(21) Appl. No.: 14/410,437

(22) PCT Filed: Aug. 10, 2013

(86) PCT No.: PCT/JP2013/071740
§ 371 (c)(1),
(2) Date: Dec. 22, 2014

(87) PCT Pub. No.: WO2014/025051
PCT Pub. Date: Feb. 13, 2014

(65) Prior Publication Data
US 2015/0157468 A1 Jun. 11, 2015

(30) Foreign Application Priority Data
Aug. 10, 2012 (JP) .................................. 2012-178914

(51) Int. Cl.
*A61F 2/46* (2006.01)
*A61B 90/35* (2016.01)
(Continued)

(52) U.S. Cl.
CPC ............ *A61F 2/4609* (2013.01); *A61B 90/11* (2016.02); *A61B 90/35* (2016.02); *A61F 2/4657* (2013.01);
(Continued)

(58) Field of Classification Search
CPC ..................................................... A61F 2/4609
(Continued)

(56) References Cited

U.S. PATENT DOCUMENTS 5,682,886 A * 11/1997 Delp .................... A61B 17/154
128/920
5,999,840 A * 12/1999 Grimson ............... G06T 3/0068
600/424
(Continued)

FOREIGN PATENT DOCUMENTS

JP 2002-345839 A 12/2002
JP 2013-169398 A 9/2013

OTHER PUBLICATIONS

PCT, "International Search Report for International Application No. PCT/JP2013/071740".
(Continued)

*Primary Examiner* — Matthew J Lawson
*Assistant Examiner* — Amy R Sipp
(74) *Attorney, Agent, or Firm* — Manabu Kanesaka

(57) ABSTRACT

CT images near the pelvis are obtained before surgery, and a three-dimensional model of a pelvis part is created on a computer. The virtual three-dimensional bone model is used to plan an installation position of a guide instrument etc., and a virtual three-dimensional surgical site model including the (Continued)

guide instrument is constructed. Subsequently, during surgery, the guide instrument is installed, and three-dimensional images of a surgical site are obtained, and a measured three-dimensional surgical site model including the guide instrument is obtained. The virtual three-dimensional surgical site model and the measured three-dimensional surgical site model are compared, and an error between an ideal installation position of the guide instrument and an actual installation position of the guide instrument is detected to guide the operator to reduce the error.

7 Claims, 8 Drawing Sheets

(51) Int. Cl.
*A61B 90/11* (2016.01)
*A61B 5/055* (2006.01)
*A61B 34/10* (2016.01)
*A61B 34/20* (2016.01)
*A61B 90/30* (2016.01)

(52) U.S. Cl.
CPC .............. *A61B 5/055* (2013.01); *A61B 90/30* (2016.02); *A61B 2034/102* (2016.02); *A61B 2034/105* (2016.02); *A61B 2034/2048* (2016.02); *A61F 2002/4632* (2013.01); *A61F 2002/4663* (2013.01)

(58) Field of Classification Search
USPC .......................................................... 600/424
See application file for complete search history.

(56) References Cited

U.S. PATENT DOCUMENTS

| | | | |
|---|---|---|---|
| 2005/0251026 A1* | 11/2005 | Stone | A61B 34/20 600/424 |
| 2007/0091464 A1 | 4/2007 | Alexay | |
| 2010/0121200 A1* | 5/2010 | Carvalho | A61B 5/0059 600/476 |
| 2012/0029581 A1 | 2/2012 | Kanekasu | |

OTHER PUBLICATIONS

"All of Total knee Arthroplasty—for safe and reliable Surgery" Medical View Co., Ltd. pp. 176-183; Feb. 5, 2007; Takuji Nakamura.

* cited by examiner

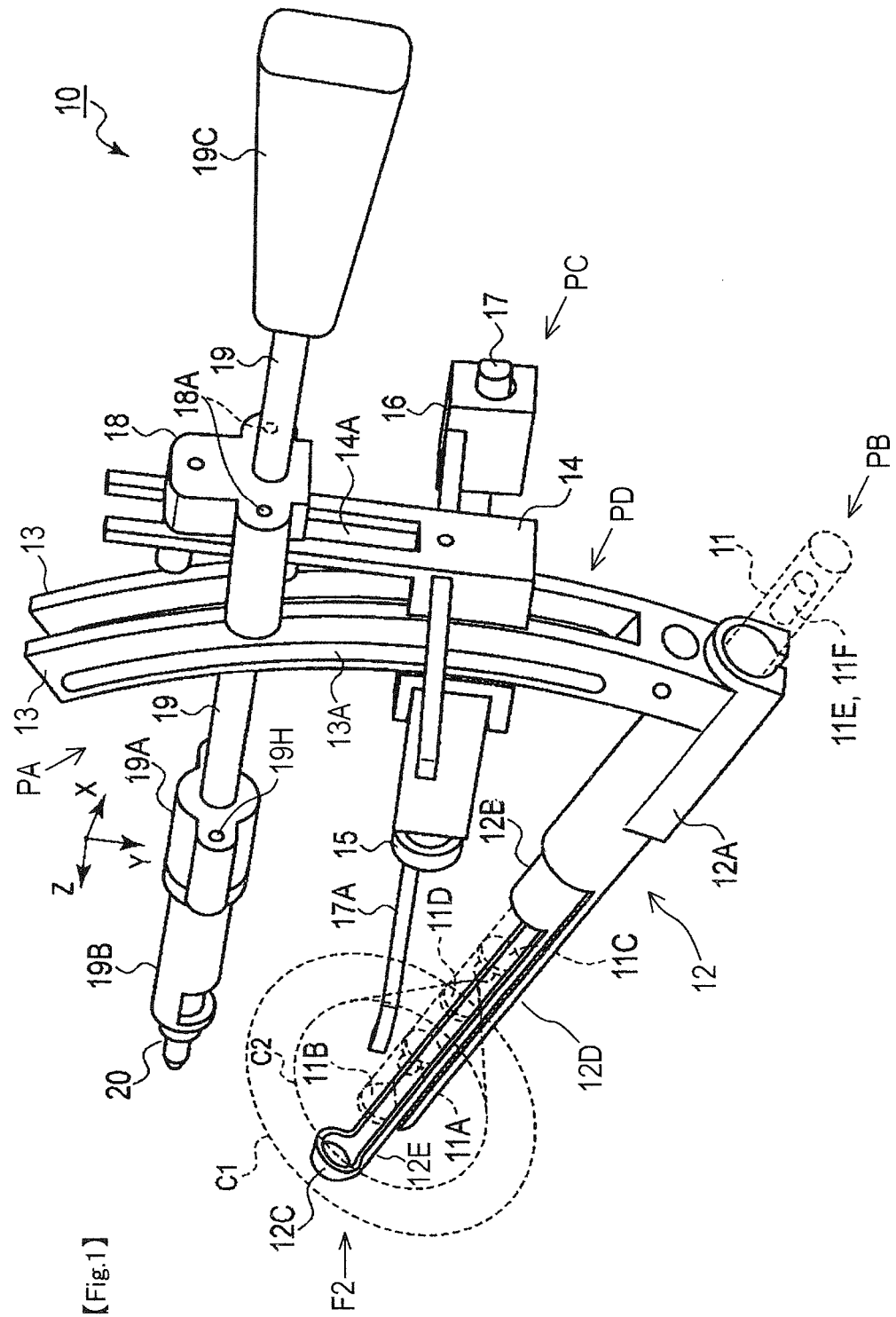
[Fig.1]

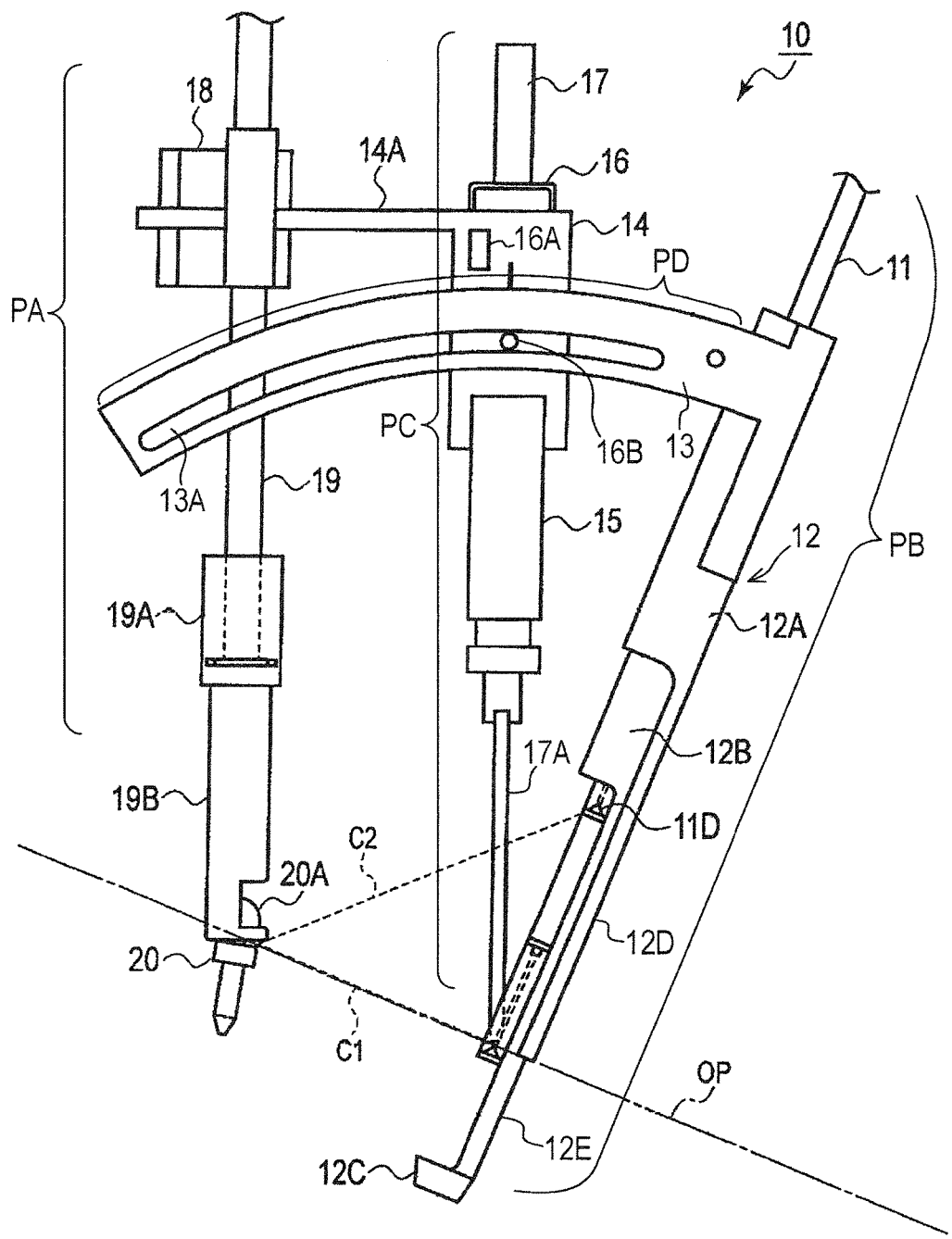
[Fig.2]

[Fig.3]
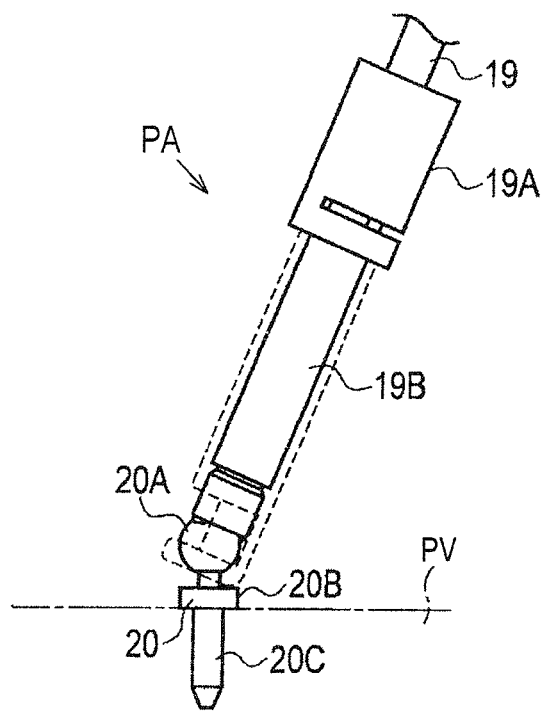

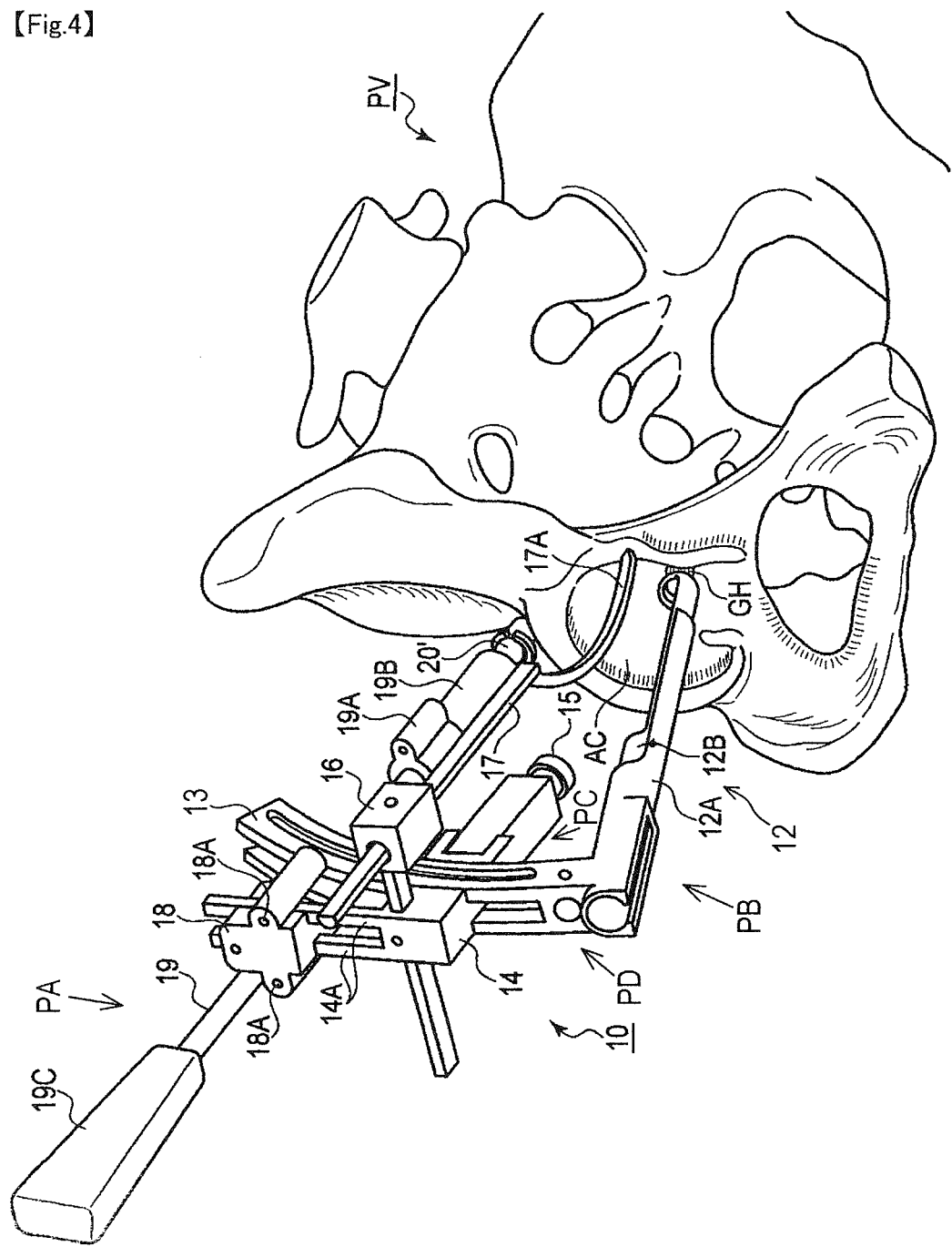
[Fig.4]

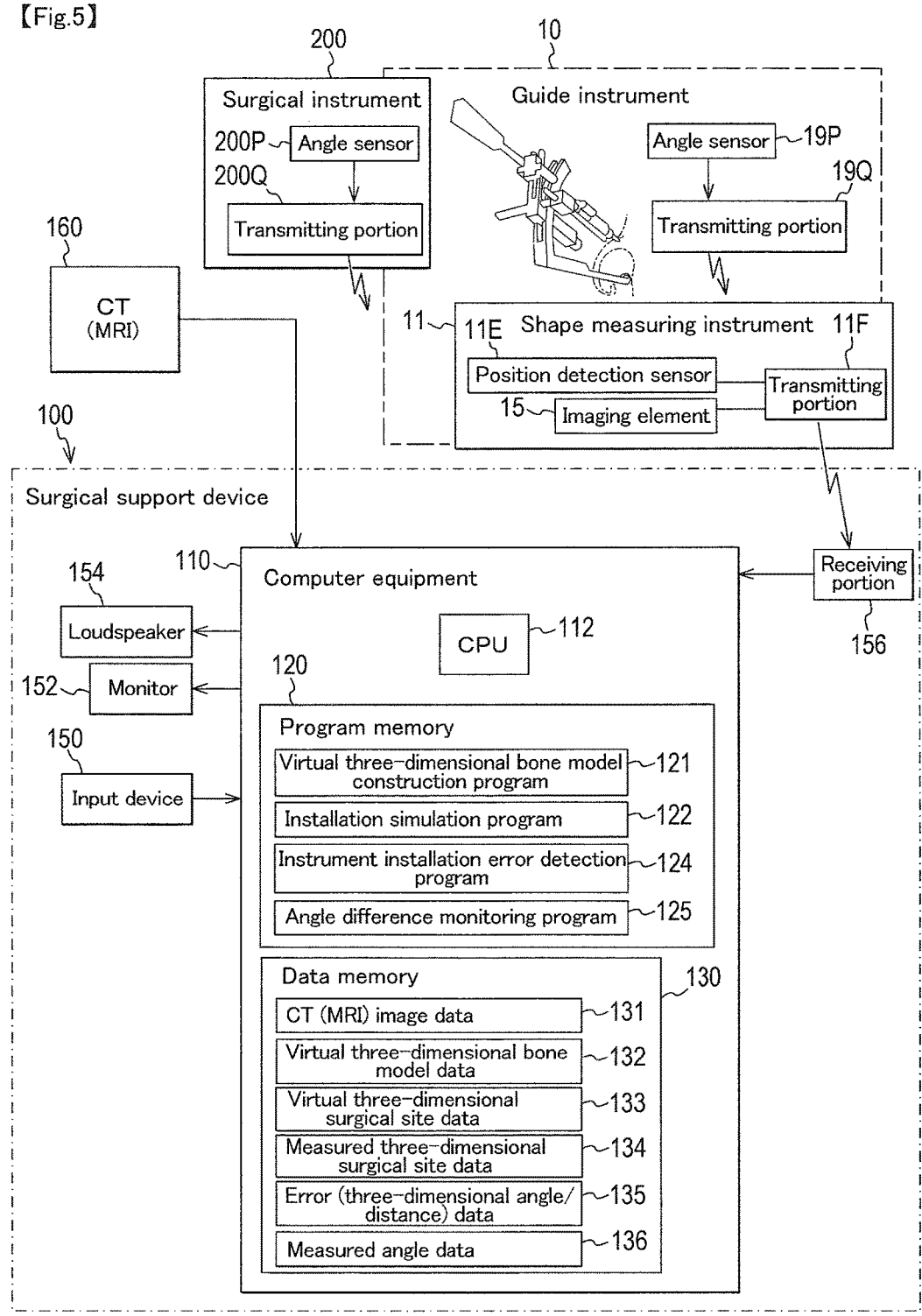

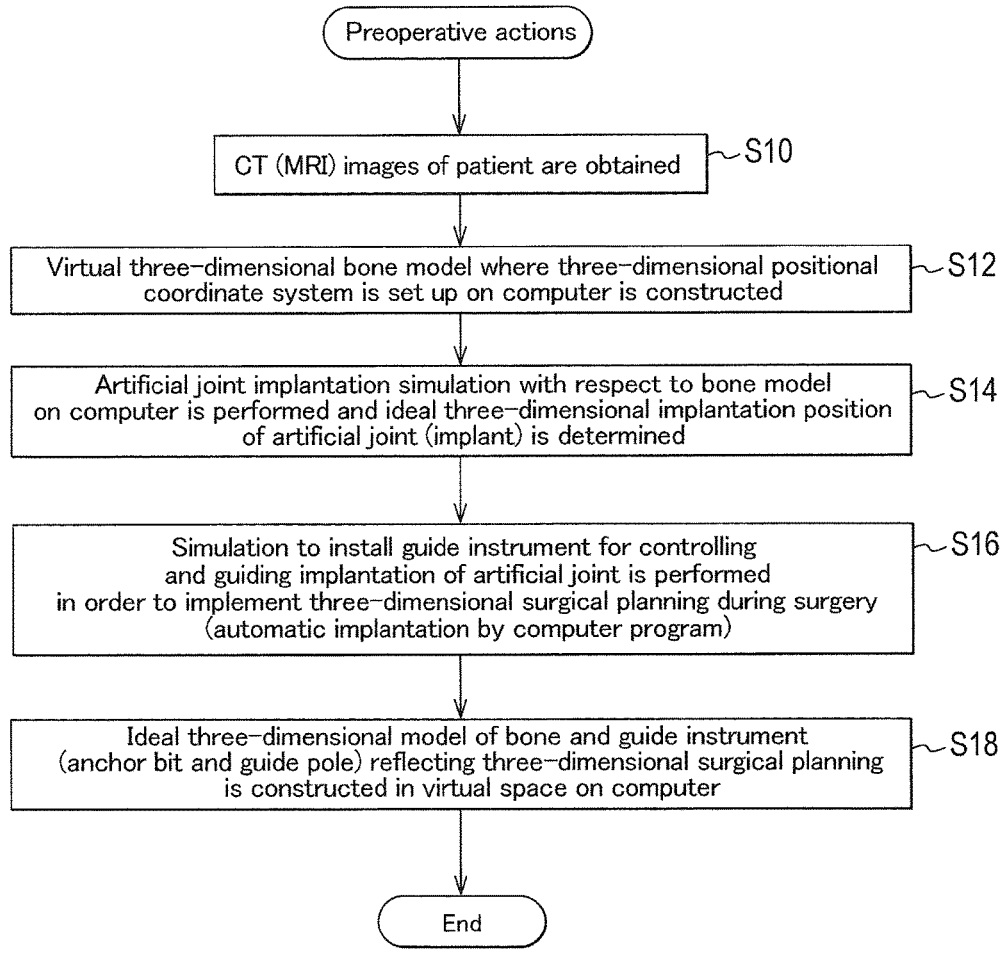
[Fig.6]

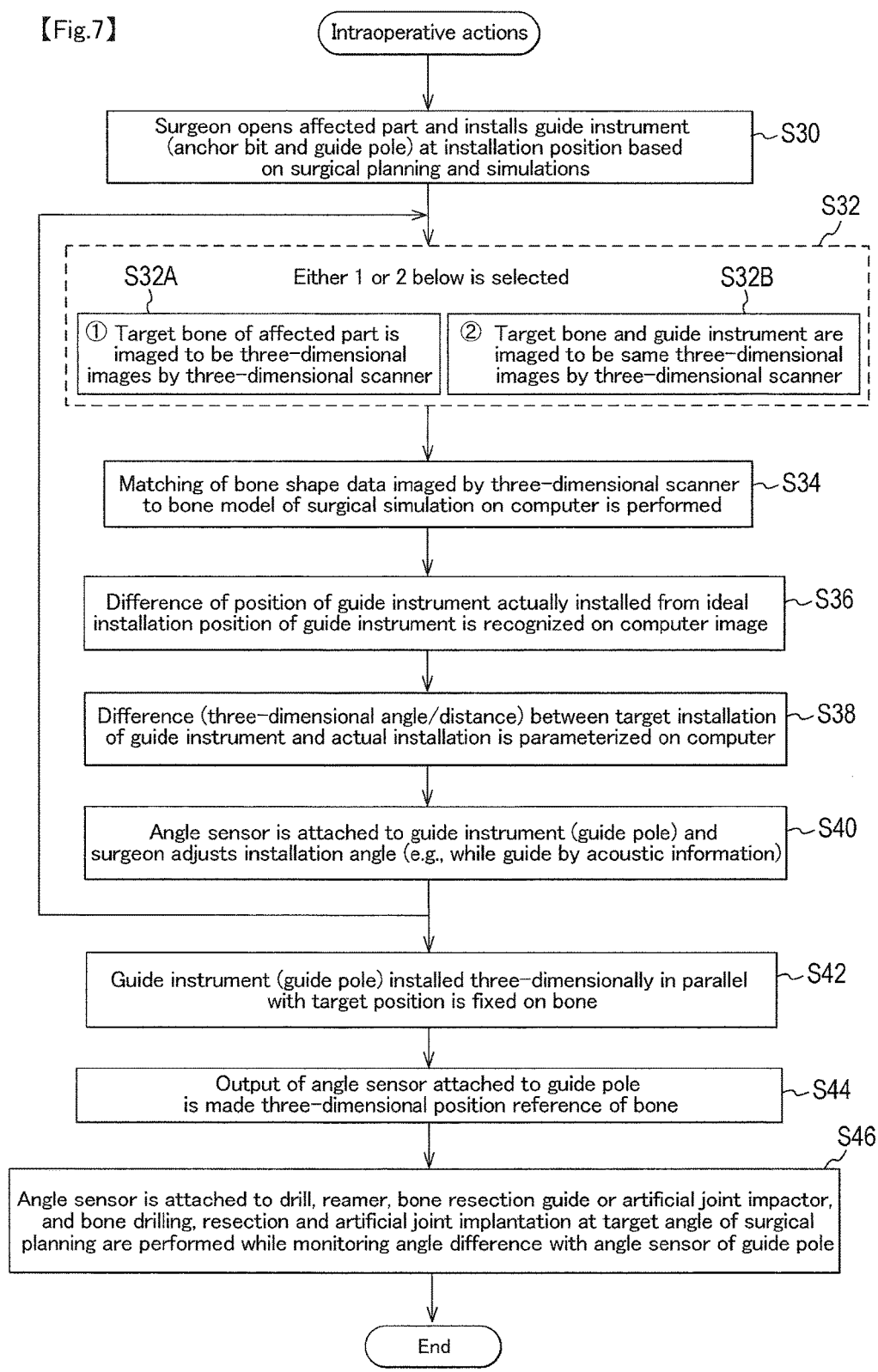

[Fig.8]    (A)
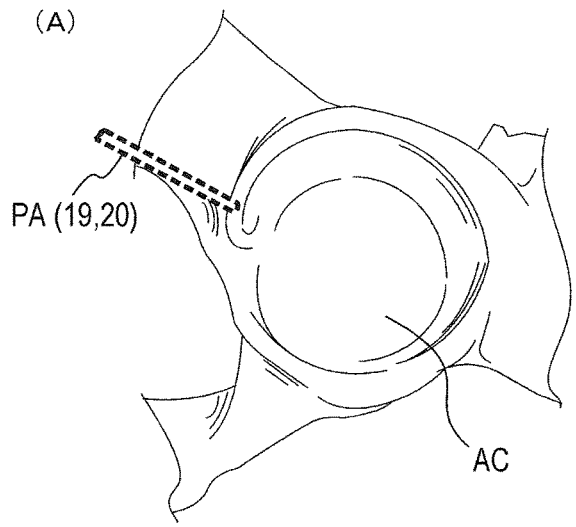
(B)
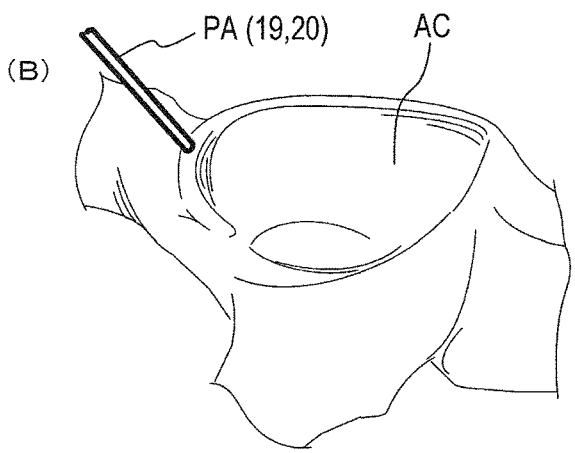
(C)
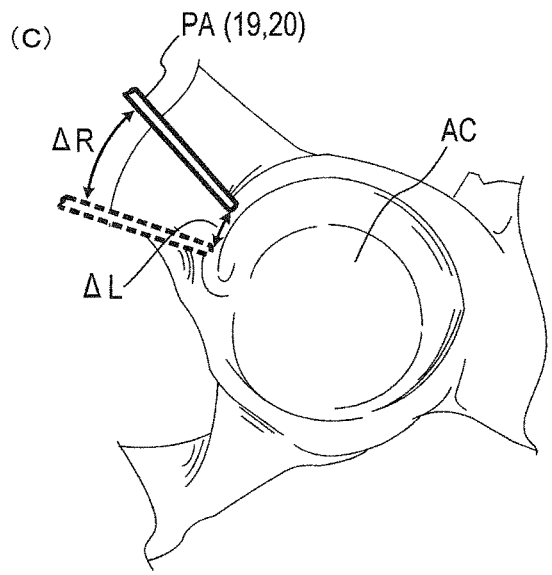

NAVIGATION DEVICE FOR JOINT REPLACEMENT AND SURGICAL SUPPORT DEVICE

RELATED APPLICATIONS

The present application is National Phase of International Application No. PCT/JP2013/071740 filed Aug. 10, 2013, and claims priority from Japanese Application No. 2012-178914, filed Aug. 10, 2012, the disclosure of which is hereby incorporated by reference herein in its entirety.

TECHNICAL FIELD

The present invention relates to a navigation device for joint replacement and a surgical support device which provide support or navigation by computer in implanting an artificial hip joint component, for example.

BACKGROUND ART

In performing an artificial joint replacement such as a knee or hip, support or navigation by computer is used to accurately implant an artificial joint component (part). Broadly speaking, there is the following technique (see Non-Patent Literature 1):
(1) A method of providing navigation by using motion information, etc., obtained by moving a joint, without using image information of a joint part by CT (Computed Tomography); and
(2) A method of providing navigation by using image information by CT to prepare a three-dimensional (3D) bone shape model, and registering it to an intraoperative bone shape.

Of these, the method (1) does not require a processing for preoperative image acquisition, but cannot be said to be satisfactory in accuracy of the navigation. On the other hand, the method (2) can prepare a highly accurate three-dimensional bone shape model by CT or MRI (magnetic resonance imaging) and improve the accuracy of the navigation.

For example, the following Patent Literature 1 "SURGICAL SUPPORT DEVICE, METHOD AND PROGRAM" is such that a three-dimensional model is created in advance based on MRI images of a patient taken before surgery, and during surgery, a surface of the patient is scanned by a laser beam and the reflected laser beam is detected, thereby measuring three-dimensional coordinates of each point on the surface and associating them with the preoperative MRI images of each point on the surface.

CITATION LIST

Patent Literature

Patent Literature 1: Japanese Published Unexamined Patent Application No. 2007-209531

Non-Patent Literature

Non-Patent Literature 1: NAKAMURA Takuji, "ALL OF TOTAL KNEEARTHROPLASTY [TKA]—for safe and reliable surgery," MEDICAL VIEW CO., LTD., published on Feb. 5, 2007, pp. 176-183

SUMMARY OF THE INVENTION

Problems to be Solved by the Invention

However, the conventional navigation technique has the following problems:

(1) A laser beam, xenon beam or infrared rays are externally applied on a patient to measure a surface shape thereof, so that the device configuration becomes large-scale and expensive;
(2) The risk of surgical stress is high and the burden on a patient is significant due to that a marker for obtaining the position of a surgical instrument is set in the bone etc.; and
(3) Manipulations require a high level of skill and the surgical time becomes long, so that the burden on an operator's side is also significant.

The present invention focuses attention on the above points, and an object thereof is to achieve downsizing and simplification of the device configuration and to reduce the price. Another object is to reduce the burden on a patient and an operator to satisfactorily perform an artificial joint replacement.

Means for Solving the Problems

A navigation device for joint replacement of the present invention is a navigation device for joint replacement using a guide instrument for guiding the position of a surgical instrument when performing a joint replacement, characterized by a bone shape calculating means configured to calculate a virtual three-dimensional bone shape of the joint part of a surgical object based on image data of a patient before surgery, a guide installation position calculating means configured to calculate an ideal installation position of the guide instrument based on the virtual three-dimensional bone shape before surgery, a bone shape obtaining means configured to obtain an actual three-dimensional bone shape of the joint part of the surgical object, during surgery, by a shape measuring instrument provided to the guide instrument actually installed, a guide installation position obtaining means configured to obtain an actual installation position of the guide instrument, during surgery, by the shape measuring instrument provided to the guide instrument actually installed and an error detecting means configured to compare the virtual three-dimensional bone shape, ideal installation position of the guide instrument, actual three-dimensional bone shape and actual installation position of the guide instrument of the respective means and to detect an error between the actual installation position and the ideal installation position of the guide instrument by shifting the virtual three-dimensional bone shape and the actual three-dimensional bone shape.

According to one of the major aspects, the present invention is characterized in that the virtual three-dimensional bone shape is calculated based on CT image data or MRI image data of the patient in the bone shape calculating means. One of the other aspects is characterized in that a laser beam is irradiated on the joint part of the surgical object by the shape measuring instrument, and the bone shape obtaining means uses reflected light of the laser beam to obtain the actual three-dimensional bone shape of the joint part of the surgical object. One of the other aspects is characterized in that a laser beam is irradiated on the joint part of the surgical object by the shape measuring instrument, and the guide installation position obtaining means uses reflected light of the laser beam to obtain the actual installation position of the guide instrument. Further another aspect is characterized in that the error detecting means uses a premise that a bone shape of a patient obtained by calculation and a bone shape of the patient actually measured are matched, and rotates and moves the images of the virtual three-dimensional bone shape and the actual three-dimensional bone shape to match the both, and detects an error between the actual installation position and the ideal installation position of the guide instrument.

A surgical support device of the present invention is a surgical support device using the aforementioned navigation device for joint replacement, characterized by position detecting means provided to the guide instrument and the surgical instrument respectively and a guiding means configured to guide an installation position of the surgical instrument during surgery so as to come closer to an ideal installation position of the surgical instrument before surgery, based on a detection result by the means configured to detect the error between the actual installation position and the ideal installation position of the guide instrument and detection results from the position detecting means.

One of the major aspects is characterized in that at least either one of a guiding sound or guiding light corresponding to the error between the installation position of the surgical instrument during surgery and the ideal installation position of the surgical instrument before surgery is output. The above and other objects, features and advantages of the present invention will become clear from the following detailed description and accompanying drawings.

Advantageous Effects of the Invention

According to the present invention, the burden on both the patient and the operator can be reduced, and an artificial joint replacement can be performed satisfactorily by performing the installation of the guide instrument following the preoperative planning.

BRIEF DESCRIPTION OF THE DRAWINGS

FIG. 1 is is a perspective view showing a guide instrument used in an embodiment of the present invention;

FIG. 2 is a side view of the above guide instrument as viewed from a direction of an arrow F2;

FIG. 3 is a diagram enlargedly showing a fixing support unit PA part of the above guide instrument;

FIG. 4 is a perspective view showing an installation example of the above guide instrument on the acetabular roof;

FIG. 5 is a block diagram showing a configuration of a surgical support device of the present invention;

FIG. 6 is a flow chart showing main steps of preoperative actions in the embodiment of the present invention;

FIG. 7 is a flow chart showing main steps of intraoperative actions in the embodiment of the present invention; and FIGS. 8(A)-8(C) are diagrams showing a relationship between a virtual three-dimensional surgical site model and a measured three-dimensional surgical site model.

MODES FOR CARRYING OUT THE INVENTION

Hereinafter, a mode for carrying out the present invention will be described in detail based on an embodiment. A brief summary thereof is as follows. The present invention can be applied to a variety of artificial joint replacements. However, a case of the pelvic acetabular roof will be described as an example. An overall operation can be summarized as follows:

(1) CT or MRI images near the pelvis are obtained before surgery and a three-dimensional model of a pelvis part is created on a computer;

(2) The above virtual three-dimensional bone model is used to plan an installation position of the guide instrument, etc., and construct a virtual three-dimensional surgical site model including the guide instrument;

(3) During surgery, the guide instrument is installed, and three-dimensional images of a surgical site are obtained, and a measured three-dimensional surgical site model including the guide instrument is obtained;

(4) The virtual three-dimensional surgical site model and the measured three-dimensional surgical site model are compared, and an error between the ideal installation position of the guide instrument and the actual installation position of the guide instrument is detected; and (5) The operator is guided so as to reduce the detected error between the installation positions of the guide instrument.

Embodiment 1

Next, an embodiment 1 of the present invention will be described. First, a guide instrument for artificial joint replacement (hereinafter, simply referred to as a "guide instrument") used in this embodiment will be described with reference to FIGS. 1 to 4. FIGS. 1 to 4 are those filed in Japanese Patent Application No. 2012-36256. A perspective view of a guide instrument 10 is shown in FIG. 1, and a side view thereof as viewed from a direction of an arrow F2 is shown in FIG. 2. In these drawings, the guide instrument 10 is broadly constituted of a. a fixing support unit PA fixing and supporting the instrument itself to the pelvis;

b. an operating unit PB to which a shape measuring instrument or a drill is attached;

c. an imaging unit PC detecting a signal from the shape measuring instrument; and d. a positioning arm unit PD for adjusting the positions of the operating unit PB and imaging unit PC with respect to the fixing support unit PA.

<Fixing Support Unit PA>

Of these, the fixing support unit PA has a ball chuck 19B held at a distal end of a guide pole 19 via a chuck holder 19A. The ball chuck 19B has a distal end attached with an anchor bit 20. The anchor bit 20 can be displaced by loosening the ball chuck 19B, and the angle between the guide pole 19 and the anchor bit 20 can be adjusted. The anchor bit 20 is a screw to be fixed to an upper outer edge portion of the acetabular roof of the pelvis. That is, the angle of the guide pole 19, furthermore the guide instrument 10 with respect to the anchor bit 20 can be adjusted optionally by loosening or fastening the ball chuck 19B and be fixed.

The other end side of the guide pole 19 is slidably sandwiched by the positioning arm unit PD, ahead of which a handle 19C is provided via a rail holder 18. The rail holder 18 holds a rail 14A of the imaging unit PC slidably, whereby the imaging unit PC is held slidably with respect to the fixing support unit PA. A pair of guide pin holes 18A are formed in the rail holder 18, and a pair of guide pin holes 19H are formed in the chuck holder 19A. There guide pin holes 18A, 19H coincide in the axial direction, and guide pins (not shown) are inserted therethrough so as to sandwich the positioning arm unit PD. Twisting of the handle side with respect to the anchor bit side is prevented by these guide pins.

FIG. 3 shows the anchor bit 20 fixed to the pelvis PV. The anchor bit 20 has a flange 20B whose upper side is a ball 20A and whose lower side is a screw 20C. The anchor bit 20 is fixed to the pelvis PV by screwing the screw 20C in near an upper end of the outer edge of the acetabular roof of the pelvis PV. After that, the ball chuck 19B is mounted on the ball 20A. The mounting angle of the ball chuck 19B at this moment allows the angle of the guide pole 19 to be adjusted.

<Operating Unit PB>

Subsequently, the operating unit PB is mainly composed of a jig holder 12. The jig holder 12 has a smaller-diameter, cylindrical moving portion 12B movable within a larger-diameter cylindrical base portion 12A. That is, the jig holder 12 is such that the cylinder of the base portion 12A and the cylinder of the moving portion 12B form a double cylindrical structure. Part of the base portion 12A is extended and serves as an extension guide 12D for guiding the movement of the moving portion 12B. Part of the moving portion 12B is also extended and serves as an extension guide 12E for guiding the movement of a shape measuring instrument 11 or drill (not shown). The moving portion 12B has a distal end formed with a ring-shaped contact portion 12C. The ring-shaped contact portion 12C is movable from an opening surface of the acetabular roof to the acetabular floor.

A surgical instrument such as the shape measuring instrument 11 or the drill (not shown) can be inserted into and detached from the cylindrical part of the moving portion 12B and additionally can move along the extension guide 12E in the direction of the ring-shaped contact portion 12C. On the other hand, the base portion 12A is joined to the positioning arm unit PD. This allows the angle between the axial direction of the guide pole 19 of the fixing support unit PA and the shape measuring instrument 11, etc., to be adjusted.

Subsequently, the shape measuring instrument 11 is a sensor which uses a laser beam for measuring
a. the shape of the acetabular roof of the patient; and
b. the position of the guide instrument 10 (specifically, the fixing position of the anchor bit 20 and the inclination of the guide pole 19). For example, an inner surface shape measuring device disclosed in Japanese Published Unexamined Patent Application No. 2007-285891 can be used. In addition, Japanese Published Unexamined Patent Application No. S63-055441, Japanese Published Unexamined Patent Application No. 2006-064690, Japanese Published Unexamined Patent Application No. 2004-101190, Japanese Published Unexamined Patent Application No. 2005-233925, Japanese Published Unexamined Patent Application No. 2005-195936 and Japanese Published Unexamined Patent Application No. H05-107037, etc., are similarly applicable. A distal end side of the cylindrical shape measuring instrument 11 is provided with a first laser oscillating portion 11A using a semiconductor laser element, a first reflecting portion 11B made of a conical mirror, a second laser oscillating portion 11C and a second reflecting portion 11D coaxially along the longitudinal direction of the cylinder.

A laser beam oscillated and output from the first laser oscillating portion 11A is reflected by the first reflecting portion 11B. As a result, the laser beam is radiated as a disk-shaped laser beam C1 extending in the entire circumferential direction on a plane orthogonal to the axial direction of the shape measuring instrument 11. On the other hand, a laser beam oscillated and output from the second laser oscillating portion 11C is reflected by the second reflecting portion 11D. As a result, the laser beam is radiated as a disk-shaped laser beam C2 extending in the entire circumferential direction on the plane orthogonal to the axial direction of the shape measuring instrument 11.

Since partially blocked by the extension guides 12D, 12E, the laser beams C1, C2 become fan-shaped but not disk-shaped. To avoid adverse effects due to reflection of the laser beams by inner wall surfaces of the extension guides 12D, 12E, it is recommended that the wall surfaces are such that they absorb the laser beam. The laser beam C2 may be a laser beam extending in a cross-like shape but not a conical shape by providing a cross-like slit between the second laser oscillating portion 11C and the second reflecting portion 11D or by a prismatic shape of the second reflecting portion 11D.

In measuring, the shape measuring instrument 11 is moved from the base portion 12A side to the ring-shaped contact portion 12C side by the moving portion 12B. Reflected light of the laser beams C1, C2 by the acetabular roof and the anchor bit 20 obtained at this moment is detected by the imaging unit PC, whereby the three-dimensional (stereoscopic) shape of the acetabular roof and the position of the anchor bit 20 are measured.

In addition, the shape measuring instrument 11 has a position detection sensor 11E for detecting the position angle of the shape measuring instrument 11 and outputting a position detection signal, and a transmitting portion 11F for transmitting an image signal obtained by the imaging portion PC and the position detection signal to a navigation device as will be described later. The position detection sensor 11E is composed of an angular velocity sensor and a three-axis acceleration sensor, for example. For the transmitting portion 11F, standards of near field communication such as a wireless LAN are used. A driving battery is incorporated in the shape measuring instrument 11.

<Imaging Unit PC>

Next, the imaging unit PC will be described. An imaging element 15 to which the foregoing reflected light of the laser beams C1, C2 by the acetabular roof, etc., is incident is attached to a slider 14 slidable along the positioning arm unit PD, while facing the direction of irradiation of the laser beams C1, C2. A pair of rails 14A are extended from the slider 14 toward the tangential direction of the positioning arm unit PD. The rail holder 18 of the fixing support unit PA can slide along these rails 14A.

The slider 14 is provided with a hook holder 16 outside the positioning arm unit PD, and a retaining hook 17 is held by this hook holder 16. The retaining hook 17 is provided in a direction that faces the center of an arc of the positioning arm unit PD (in a direction orthogonal to the arc), and the retaining hook 17 has a distal end formed with a curved portion 17A (see FIG. 4). By inserting such retaining hook 17 into a peripheral edge of the acetabular roof from an open wound in surgery, the visual field of an affected part is secured and imaging by the imaging element 15 can be performed satisfactorily. A distance between the slider 14 and the hook holder 16 can be adjusted by a support rod 16A. The axial direction of the retaining hook 17 is the same as that of the guide pole 19.

<Positioning Arm Unit PD>

Next, the positioning arm unit PD is an arc with the center of a distal end of the extension guide 12D of the base portion 12A in the aforementioned operating unit PB (see FIG. 2), and has a pair of arc-shaped arms 13 provided in parallel in an arc shape. One end portions of the arc-shaped arms 13 are connected and fixed to the jig holder 12 of the operating unit PB. An arc-shaped slit 13A is formed in lateral surfaces of the arc-shaped arms 13. A pin 16B protruded from a lateral surface of the slider 14 of the aforementioned imaging unit PC enters this slit 13A (see FIG. 2). This pin 16B abuts against the slit 13A and slides, whereby the slider 14 is held slidably along the arc-shaped arms 13.

The above points can be summarized as follows:
a. The fixing support unit PA can move in parallel with the imaging unit PC along the rail 14A;

b. The imaging unit PC can move circularly along the positioning arm unit PD. This allows the imaging unit PC to image the distal end part of the operating unit PB in any position; and c. The fixing support unit PA can change the angle with respect to the anchor bit 20 at the distal end. Focusing on the anchor bit 20, the overall inclination of the guide instrument 10 can be adjusted.

Further, the following fixtures using screws, etc., are provided as appropriate in order to fix the position of each part:

a. The position of the slider 14 with respect to the arc-shaped arms 13 is fixed;

b. The distance between the slider 14 and the retaining hook 17 is fixed; and c. The position of the rail holder 18 with respect to the rail 14A is fixed.

The aforementioned state shown in FIG. 2 shows an example of the physical relationship of each part when letting an opening plane of the acetabular roof substantially hemispherically recessed be OP. The anchor bit 20 of the fixing support unit PA is positioned on the opening plane OP. The ring-shaped contact portion 12C at the distal end of the operating unit PB is positioned within the acetabular roof lower than the opening plane OP. The imaging element 15 of the imaging unit PC captures the distal end part of the shape measuring instrument 11 in the visual field, and the distal end of the curved portion 17A of the retaining hook 17 is positioned on the opening plane OP, thereby securing the visual field of the imaging element 15. The state of the guide instrument 10 installed with respect to the pelvis PV is shown in FIG. 4.

<Navigation Device>

Next, a surgical support device 100 using the aforementioned guide instrument will be described with reference to a block diagram of FIG. 5. In FIG. 5, the surgical support device 100 is mainly composed of computer equipment 110 such as a personal computer. Of these, FIG. 5 shows a. a CPU 112 as an arithmetic unit;

b. a program memory 120 storing a program executed by the CPU 112; and c. a data memory 130 storing data externally obtained or data after calculation as particularly pertaining to the present invention. As the program memory 120 and the data memory 130, a hard disk is used, for example. Further, to the computer equipment 110, d. an input device 150 such as a keyboard or a mouse;

e. a monitor 152 for displaying an image or data;

f. a speaker 154 for outputting a guiding sound (an alarm) in surgery;

g. a receiving portion 156 for receiving a signal sent from the aforementioned guide instrument 10 or a surgical instrument 200 such as a drill; and h. a CT (MRI) apparatus 160 are connected via appropriate interfaces. A printer, a disk drive, etc., are connected if necessary.

Angle sensors 19P, 200P are respectively attached to the guide pole 19 of the guide instrument 10 and the surgical instrument 200 such as the drill in surgery. Detection signals are received by the receiving portion 156 via transmitting portions 19Q, 200Q.

Subsequently, the program stored in the program memory 120 and the data stored in the data memory 130 will be described.

a. CT image data 131 is CT image data of a patient picked up by the CT apparatus 160 and is data shown in a coordinate system of the CT apparatus 160, in a manner, a CT coordinate system. The CT image data 131 may be MRI images.

b. A virtual three-dimensional bone model construction program 121 is a program for calculating and virtually constructing a three-dimensional shape of the pelvis part centering the acetabular roof of the patient based on the CT image data 131. The calculated three-dimensional shape data is saved as virtual three-dimensional bone model data 132 in the data memory 130.

c. An installation simulation program 122 is a program for determining the installation position of the guide instrument 10, specifically, the ideal installation position of the anchor bit 20 and the orientation of the guide pole 19 of the fixing support unit PA, based on the virtual three-dimensional bone model data 132. The data of the determined ideal position of the anchor bit 20 and orientation of the guide pole 19 is added to the virtual three-dimensional bone model data 132 and is saved as virtual three-dimensional surgical site data 133 in the data memory 130.

d. Measured three-dimensional surgical site data 134 is three-dimensional data of the bone shape and installed guide pole 19 and anchor bit 20 picked up by the imaging element 15 by using the shape measuring instrument 11 of the guide instrument 10 in actual surgery.

e. An instrument installation error detection program 124 is a program for comparing the virtual three-dimensional surgical site data 133 obtained on the computer and the measured three-dimensional surgical site data 134 obtained in surgery and for detecting an error of installation of the guide instrument 10, that is, detecting the inclination of the guide pole 19 and the displacement of the anchor bit 20, which are stored as angle and distance error data 135 in the data memory 130.

f. Measured angle data 136 is data showing detection results of the angle sensor 19P installed on the guide pole 19 in surgery and the angle sensor 200P installed on the surgical instrument 200 such as the drill.

g. An angle difference monitoring program 125 is a program for making reference to the measured angle data 136 and alarm-outputting comparison results.

Next, the prementioned shape measuring instrument 11 of the guide instrument 10 is provided with the position detection sensor 11E, and position change information detected thereby is transmitted from the transmitting portion 11F together with the imaging signal of the imaging element 15 and then received by the computer equipment 110 via the receiving portion 156. The guide pole 19 and the surgical instrument 200 such as the drill are respectively provided with the angle sensors 19P, 200P in surgery. Their detection signals are transmitted to the receiving portion 156 by the transmitting portions 19Q, 200Q, and taken into the computer equipment 110.

<Preoperative Actions>

Next, among the actions of the foregoing embodiment performed before surgery will be described, referring to FIG. 6, as well. First, CT images near the pelvis of the patient are obtained by the CT apparatus 160 and are saved as the CT image data 131 in the data memory 130 of the computer equipment 110 (step S10). Next, the virtual three-dimensional bone model construction program 121 is executed by the CPU 112 in the computer equipment 110, and a three-dimensional bone model is virtually constructed on the computer based on the CT image data 131 (step S12). The coordinate system showing the virtual three-dimensional bone model is a three-dimensional positional coordinate system set up on the computer. The constructed virtual three-dimensional bone model data 132 is stored in the data memory 130.

Next, the installation simulation program 122 is executed by the CPU 112. An artificial joint implantation simulation is performed while making reference to the virtual three-dimensional bone model, and an optimum installation position of the guide instrument 10 is determined. Procedural steps of this determination are as follows:

a. First, the virtual three-dimensional bone model data 132 is used to perform an artificial joint implantation simulation, and an ideal three-dimensional implantation position of the artificial joint is determined (step S14). This operation is performed in a virtual space by the operator (surgeon) while referring to the monitor 152;

b. Subsequently, the three-dimensional surgical planning is implemented during surgery, and a simulation to install the guide instrument 10 is performed such that the determined ideal three-dimensional implantation position of the artificial joint can be reproduced in surgery (step S16); and c. Subsequently, a three-dimensional model of the position on the three-dimensional bone model having been constructed in the virtual space on the computer, which position was obtained at the above step, that is, an ideal three-dimensional model of the bone and the guide instrument 10 (the anchor bit 20 and the guide pole 19) reflecting the three-dimensional surgical planning is constructed (step S18).

The data of the ideal position of the anchor bit 20 and the ideal orientation of the guide pole 19 determined in the above manner is added to the virtual three-dimensional bone model data 132 and is saved as the virtual three-dimensional surgical site data 133 in the data memory 130. As the above mentioned virtual three-dimensional bone model construction program 121 and the installation simulation program 122, software "HipKnee" manufactured by LEXI Co., Ltd. can be used, for example.

<Intraoperative Actions>

Next, intraoperative actions in actual replacement will be described. Procedural steps thereof are shown in FIG. 7. A surgeon responsible for the surgery opens an affected part and installs the anchor bit 20 and guide pole 19 of the guide instrument 10 having been completely sterilized at the installation position based on the foregoing surgical planning and simulations (step S30).

The state thereof is shown in FIG. 4. FIG. 4 shows the pelvis PV part broadly, but the periphery of the acetabular roof can only be seen from a small incised part in actual surgery. The anchor bit 20 provided at the distal end of the guide pole 19 of the fixing support unit PA of the guide instrument 10 is fixed at the upper outer edge of the acetabular roof AC, based on the preoperative planning. Ideally, the anchor bit 20 is fixed at the position determined in the preoperative planning at this moment, but the practical installation position includes an error.

Subsequently, the laser beams C1, C2 are output from the shape measuring instrument 11, and the acetabular roof AC part is imaged to obtain three-dimensional images (step S32). A detailed description is given. First, to obtain the three-dimensional images of the acetabular roof AC part satisfactorily, the positioning of the operating unit PB is performed so as for the ring-shaped contact portion 12C at the distal end side of the shape measuring instrument 11 to be placed in the center of the acetabular roof AC. Subsequently, the laser beam C1 extending in the disk shape by the first laser oscillating portion 11A and the first reflecting portion 11B and the laser beam C2 extending in the conical shape (or the cross-like shape) by the second laser oscillating portion 11C and the second reflecting portion 11D are radiated alternately in a time sharing manner. Specifically, the laser beams are radiated at an interval of, for example, 0.1 seconds according to the continuous shooting speed of the imaging element 15. The obtained picked-up image data is consecutively transmitted to the computer equipment 110 by the transmitting portion 11F together with the position signal detected by the position detection sensor 11E. These image signal by means of the shape measuring instrument 11 and position signal by means of the position detection sensor 11E are stored as the measured three-dimensional surgical site data 134 in the data memory 130. As a specific technique for obtaining the measured three-dimensional surgical site data 134 by using the shape measuring instrument 11, "INNER SURFACE SHAPE MEASURING METHOD AND MEASURING DEVICE USING THIS METHOD" disclosed in Japanese Published Unexamined Patent Application No. 2007-285891, for example is preferred.

In the computer equipment 110, the installation error detection program 124 is executed by the CPU 112 and data matching between the virtual three-dimensional surgical site data 133 and the measured three-dimensional surgical site data 134 is performed (step S34). The difference between the ideal installation position of the guide instrument 10 and the installation position of the guide instrument 10 actually installed is then recognized (step S36) and parameterized (step S38).

The state thereof is shown in FIG. 8. FIG. 8A shows the position of the fixing support unit PA (the anchor bit 20 and the guide pole 19) of the guide instrument 10 having been set in the preoperative planning, on the virtual three-dimensional bone model. FIG. 8B shows the actual position of the fixing support unit PA during surgery. Since the shapes of the acetabular roofs AC are supposed to match between the virtual three-dimensional surgical site data 133 and the measured three-dimensional surgical site data 134, the images are rotated and moved so as to match the both. FIG. 8C shows the state of the acetabular roofs AC matched. There exist $\Delta L$ in distance of the anchor bit 20 and $\Delta R$ in angle of the guide pole 19 between the virtual installation position and the actual installation position of the fixing support unit PA. These distance difference $\Delta L$ and angle difference $\Delta R$ are stored as the error data 135 in the data memory 130.

In the computer equipment 110, the angle difference monitoring program 125 is executed by the CPU 112 and the measured angle data 136 is referred to. A guiding sound is thereby output as acoustic information from the speaker 154. The operator adjusts the position of the fixing support unit PA (the anchor bit 20 and the guide pole 19) of the guide instrument 10 while using the guiding sound as a reference. Specifically, the position of the rail holder 18 with respect to the slider 14 of the guide instrument 10, the position of the slider 14 with respect to the arc-shaped arms 13, the position of the retaining hook 17 with respect to the hook holder 16 and the position of the hook holder 16 with respect to the slider 14 are adjusted to be positioned as planned before surgery. In this state, a signal output of the angle sensor 19P attached to the guide pole 19 indicates the position reference of the guide instrument 10 with respect to the acetabular roof AC (step S44).

Subsequently, the surgical instrument 200 (see FIG. 5) such as a drill, a reamer, a bone resection guide or an artificial joint impactor is attached to the jig holder 12 of the guide instrument 10 together with the angle sensor 200P and the transmitting portion 200Q, instead of the aforementioned shape measuring instrument 11. The position detection sensor 11E and transmitting portion 11F attached to the shape measuring instrument 11 may be used. In the computer equipment 110, on the other hand, an output of the angle sensor 19P of the guide pole 19 and an output of the angle sensor 200P of the surgical instrument 200 received by the receiving portion 156 are stored as the measured angle data 136 in the data memory 130. In the CPU 112, the angle difference monitoring program 125 is running, and the outputs of the angle sensors are compared and the angle difference between the both is monitored (step S46). The guiding sound is output from the speaker 154 such that the surgical instrument 200 takes a target angle of the preoperative planning. Following this guiding sound, procedures such as bone drilling, resection and artificial joint implantation are performed, wherewith the artificial joint replacement in line with the preoperative planning is performed. As a specific technique for position recognition using the outputs of two angle sensors, the invention of Japanese Published Unexamined Patent Application No. 2008-295527, "BODY INCLINATION ANGLE MEASURING INSTRUMENT AND BODY TWIST ANGLE MEASURING INSTRUMENT" can be applied, for example.

As described above, there are the following advantageous effects according to the present embodiment:
(1) The downsizing of the navigation device can be achieved without requiring a large-scale device such as for externally applying a laser beam on the patient;
(2) There is no need to place on the bone a marker for obtaining the position of the surgical instrument, which is minimally invasive, and a reduction in burden on the patient can be achieved; and
(3) A high level of skill in operating the instrument is unnecessary, and the burden on the operator is also reduced, and the artificial joint replacement can be performed satisfactorily.

The present invention should not be limited to the aforementioned embodiment, and various modifications can be made without departing from the scope and spirit of the present invention. For example, the following are also included:
(1) In the foregoing embodiment, the case in which the present invention is applied to the artificial joint replacement of the hip joint is shown. However, the present invention can be similarly applied to an artificial joint replacement of other joint parts;
(2) The angle sensors are used in the foregoing embodiment, but a variety of sensors for detecting the position such as an angular velocity sensor or an acceleration sensor can be used. For example, the acceleration sensor can be used in a hip joint surgery;
(3) The three-dimensional bone model is constructed in the virtual space on the computer from the CT or MRI images in the foregoing embodiment. However, a real-size bone model of the pelvis part may be made of, for example, acrylic photocurable resin, ABS resin or gypsum powder, etc., and by using this, the preoperative planning may be implemented;
(4) The signal transmission and reception between each sensor and the computer is performed wirelessly in the foregoing embodiment. However, the present invention should not preclude the performance of wired transmission and reception; and
(5) The guiding sound is output from the speaker 154 and the positioning of the guide instrument 10 is performed following this guiding sound in the foregoing embodiment. However, the positioning may be guided by light, and furthermore, both the guiding sound and guiding light may be used. For example, it is in such a manner that the guide instrument 10 is provided with an LED (a light-emitting diode), by which instructions on the positioning direction are given.

INDUSTRIAL APPLICABILITY

According to the present invention, the downsizing, simplification and price reduction of the navigation device can be achieved, and the burden on the patient and the operator can be reduced. Therefore, the present invention is suitable for a variety of artificial joint replacements.

DESCRIPTION OF NUMERAL SYMBOLS

10: Guide instrument
11: Shape measuring instrument
11A: First laser oscillating portion
11B: First reflecting portion
11C: Second laser oscillating portion
11D: Second reflecting portion
11E: Position detection sensor
11F: transmitting portion
12: Jig holder
12A: Base portion
12B: Moving portion
12C: Ring-shaped contact portion
12D, 12E: Extension guide
13: Arc-shaped arm
13A: Slit
14: Slider
14A: Rail
15: Imaging element
16: Hook holder
16A: Support rod
16B: Pin
17: Retaining hook
17A: Curved portion
18: Rail holder
18A, 19H: Guide pin hole
19: Guide pole
19A: Chuck holder
19B: Ball chuck
19C: Handle
19H: Guide pin hole
19P: Angle sensor
19Q: Transmitting portion
20: Anchor bit
20A: Ball
20B: Flange
20C: Screw
42: Step
100: Surgical support device
110: Computer equipment
112: CPU
120: Program memory
121: Virtual three-dimensional bone model construction program
122: Installation simulation program
124: Instrument installation error detection program
125: Angle difference monitoring program
130: Data memory
131: CT image data
132: Virtual three-dimensional bone model data
133: Virtual three-dimensional surgical site data
134: Measured three-dimensional surgical site data
135: Error data 136: Measured angle data
150: Input device
152: Monitor
154: Speaker
156: Receiving portion
160: CT apparatus
200: Surgical instrument
200P: Angle sensor
200Q: Transmitting portion
AC: Acetabular roof
C1, C2: Laser beam
PA: Fixing support unit
PB: Operating unit
PC: Imaging unit
PD: Positioning arm unit
PV: Pelvis

What is claimed is:

1. A navigation device for joint replacement, the navigation device comprising:
   a guide instrument for guiding a position of a surgical instrument when performing a joint replacement, the guide instrument having
      a fixing support unit for fixing and supporting the guide instrument to a surgical object,
      an operating unit to which the surgical instrument or a shape measuring instrument is detachably attached,
      an imaging unit slidably held by the fixing support unit for detecting signals from the shape measuring instrument when the shape measuring instrument is attached to the operating unit, and
      a positioning arm unit joined to the operating unit for adjusting positions of the operating unit and the imaging unit relative to a position of the fixing support unit;
   a bone shape calculating means configured to calculate a virtual three-dimensional bone shape of a joint part of a surgical object based on image data of a patient before surgery;
   a guide installation position calculating means configured to calculate an ideal installation position of the guide instrument based on the virtual three-dimensional bone shape before surgery;
   a bone shape obtaining means configured to obtain an actual three-dimensional bone shape of the joint part of the surgical object, during surgery, by the shape measuring instrument attached to the guide instrument actually installed;
   a guide installation position obtaining means configured to obtain an actual installation position of the guide instrument, during surgery, by the shape measuring instrument attached to the guide instrument actually installed; and
   an error detecting means configured to compare the virtual three-dimensional bone shape, ideal installation position of the guide instrument, actual three-dimensional bone shape and actual installation position of the guide instrument of the respective means, and to detect an error between the actual installation position and the ideal installation position of the guide instrument by shifting the actual installation position to align with the ideal installation position.

2. The navigation device for joint replacement according to claim 1, wherein the virtual three-dimensional bone shape is calculated based on CT image data or MRI image data of the patient in the bone shape calculating means.

3. The navigation device for joint replacement according to claim 1, wherein a laser beam is irradiated on the joint part of the surgical object by the shape measuring instrument, and the bone shape obtaining means uses reflected light of the laser beam to obtain the actual three-dimensional bone shape of the joint part of the surgical object.

4. The navigation device for joint replacement according to claim 1, wherein a laser beam is irradiated on the joint part of the surgical object by the shape measuring instrument, and the guide installation position obtaining means uses reflected light of the laser beam to obtain the actual installation position of the guide instrument.

5. The navigation device for joint replacement according to claim 1, wherein the error detecting means uses a premise that a bone shape of a patient obtained by calculation and a bone shape of the patient actually measured are matched, and the error detecting means rotates and moves images of the virtual three-dimensional bone shape and the actual three-dimensional bone shape to match the shapes, and detects the error between the actual installation position and the ideal installation position of the guide instrument.

6. A surgical support device comprising:
   the navigation device for joint replacement according to claim 1;
   a position detecting means provided to the guide instrument and the surgical instrument respectively; and
   a portion of the guide instrument configured to guide an installation position of the surgical instrument during surgery so as to come closer to an ideal installation position of the surgical instrument before surgery, based on a detection result by the error detecting means configured to detect the error between the actual installation position and the ideal installation position of the guide instrument, and detection results from the position detecting means.

7. The surgical support device according to claim 6, wherein the portion of the guide instrument outputs at least either one of a guiding sound or guiding light, corresponding to the detection result between the installation position of the surgical instrument during surgery and the ideal installation position of the surgical instrument before surgery.

* * * * *